US011053181B2

(12) United States Patent
Li

(10) Patent No.: US 11,053,181 B2
(45) Date of Patent: Jul. 6, 2021

(54) ZEOLITIC CATALYTIC CONVERSION OF ALCOHOLS TO OLEFINS

(71) Applicant: UT-Battelle, LLC, Oak Ridge, TN (US)

(72) Inventor: Zhenglong Li, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 16/530,397

(22) Filed: Aug. 2, 2019

(65) Prior Publication Data

US 2020/0048170 A1 Feb. 13, 2020

Related U.S. Application Data

(60) Provisional application No. 62/716,581, filed on Aug. 9, 2018.

(51) Int. Cl.
| | |
|---|---|
| *B01J 29/70* | (2006.01) |
| *C07C 11/02* | (2006.01) |
| *B01J 29/06* | (2006.01) |
| *C07C 1/24* | (2006.01) |
| *B01J 29/72* | (2006.01) |
| *B01J 29/76* | (2006.01) |
| *B01J 29/74* | (2006.01) |
| *B01J 37/02* | (2006.01) |
| *B01J 35/00* | (2006.01) |
| *B01J 37/00* | (2006.01) |
| *B01J 37/04* | (2006.01) |
| *B01J 37/30* | (2006.01) |
| *C07C 1/20* | (2006.01) |
| *C07C 11/06* | (2006.01) |
| *C07C 11/04* | (2006.01) |
| *C07C 11/16* | (2006.01) |
| *C07C 11/167* | (2006.01) |
| *C07C 11/12* | (2006.01) |
| *C07C 11/08* | (2006.01) |

(52) U.S. Cl.
CPC .............. *C07C 11/02* (2013.01); *B01J 29/06* (2013.01); *B01J 29/7007* (2013.01); *B01J 29/7057* (2013.01); *B01J 29/7215* (2013.01); *B01J 29/7415* (2013.01); *B01J 29/7615* (2013.01); *B01J 35/0006* (2013.01); *B01J 35/0073* (2013.01); *B01J 37/0036* (2013.01); *B01J 37/0201* (2013.01); *B01J 37/0207* (2013.01); *B01J 37/04* (2013.01); *B01J 37/30* (2013.01); *C07C 1/20* (2013.01); *C07C 1/24* (2013.01); *C07C 11/04* (2013.01); *C07C 11/06* (2013.01); *C07C 11/08* (2013.01); *C07C 11/12* (2013.01); *C07C 11/16* (2013.01); *C07C 11/167* (2013.01); *B01J 2229/16* (2013.01); *B01J 2229/18* (2013.01); *B01J 2229/186* (2013.01); *B01J 2229/20* (2013.01); *B01J 2229/37* (2013.01); *C07C 2529/74* (2013.01); *C07C 2529/76* (2013.01); *C07C 2529/78* (2013.01)

(58) Field of Classification Search
CPC ................ B01J 29/7007; B01J 29/7057; B01J 29/7215; B01J 29/7415; B01J 29/7615; B01J 2229/20; B01J 2229/37; B01J 2229/16; B01J 2229/18; B01J 2229/186; B01J 35/0006; B01J 35/0073; B01J 37/0201; B01J 37/0207; B01J 37/0036; B01J 37/04; B01J 37/30; C07C 2529/74; C07C 2529/76; C07C 2529/78; C07C 1/20; C07C 1/24; C07C 11/02; C07C 11/04; C07C 11/06; C07C 11/08; C07C 11/12; C07C 11/16; C07C 11/167
USPC ............... 502/60, 63, 64, 65, 66, 69, 73, 74; 585/601, 603, 606, 609, 638, 639, 640, 585/310
See application file for complete search history.

(56) References Cited

U.S. PATENT DOCUMENTS

| | | |
|---|---|---|
| 4,025,571 A | 5/1977 | Lago |
| 4,608,355 A | 8/1986 | Chu |
| 4,690,903 A | 9/1987 | Chen et al. |
| 4,727,214 A | 2/1988 | Uytterhoeven et al. |
| 4,851,606 A | 7/1989 | Ragonese et al. |
| 4,899,015 A | 2/1990 | Harandi et al. |
| 5,773,676 A | 6/1998 | Drake et al. |
| 6,046,373 A | 4/2000 | Sun |
| 7,872,054 B2 | 1/2011 | Cortright et al. |
| 9,181,493 B2 | 11/2015 | Narula et al. |
| 9,533,921 B2 | 1/2017 | Narula et al. |
| 9,938,467 B2 | 4/2018 | Narula et al. |
| 2007/0087934 A1* | 4/2007 | Martens ................... C10G 3/45 502/214 |
| 2009/0124842 A1* | 5/2009 | Reagan ................... C10G 11/18 585/653 |
| 2010/0304455 A1 | 12/2010 | Inoue et al. |
| 2017/0044446 A1* | 2/2017 | Cross, Jr. ............... C10G 57/00 |
| 2017/0355649 A1 | 6/2017 | Narula et al. |

* cited by examiner

*Primary Examiner* — Elizabeth D Wood
(74) *Attorney, Agent, or Firm* — Scully, Scott, Murphy & Presser, P.C.

(57) ABSTRACT

A catalyst composition for converting an alcohol to olefins, the catalyst composition comprising the following components: (a) beta zeolite; (b) at least one element selected from the group consisting of zinc, magnesium, calcium, strontium, sodium, and potassium; and (c) at least one element selected from the group consisting of hafnium, yttrium, zirconium, tantalum, niobium, and tin; wherein the components (b) and (c) are independently within or on a surface of said beta zeolite. The catalyst may also further include component (d), which is copper or silver. Also described herein is a method for converting an alcohol to one or more olefinic compounds, the method comprising contacting the alcohol with a catalyst at a temperature of at least 100° C. and up to 500° C. to result in the alcohol being converted to the one or more olefinic compounds.

27 Claims, No Drawings

ZEOLITIC CATALYTIC CONVERSION OF ALCOHOLS TO OLEFINS

CROSS REFERENCE TO RELATED APPLICATION

The present application claims benefit of U.S. Provisional Application No. 62/716,581, filed on Aug. 9, 2018, all of the contents of which are incorporated herein by reference.

GOVERNMENT SUPPORT

This invention was made with government support under Prime Contract No. DE-AC05-00OR22725 awarded by the U.S. Department of Energy. The government has certain rights in the invention.

FIELD OF THE INVENTION

The present invention relates, generally, to the catalytic conversion of alcohols to hydrocarbons, and more particularly, to zeolite-based catalytic methods for conversion of alcohols, such as ethanol, to olefins.

BACKGROUND OF THE INVENTION

As part of a continuing effort in finding more cost-effective, environmentally friendly, and independent solutions to fuel production and consumption, the conversion of ethanol and other alcohols to hydrocarbons has become an active field of study. Ethanol, in particular, is of particular interest as an alcohol feedstock because it has the potential to be made in large quantity by renewable means (e.g., fermentation of biomass). However, several hurdles need to be overcome before such a process can become industrially feasible for producing olefins and hydrocarbon blendstocks of substantial equivalence to jet fuel, gasoline and other petrochemical fuels.

A few ethanol conversion technologies for jet fuel production are currently available. The first technology is via ethanol dehydration, oligomerization, and hydrogenation. This technology requires significant energy input due to the endothermic dehydration reaction. The carbon efficiency for producing the desired jet fuel is still very low, and the ethylene oligomerization step is usually very costly. The second approach is to convert ethanol to isobutylene via a mixed oxide catalyst, followed by oligomerization and hydrogenation. The major limitation in the foregoing process is the low carbon efficiency due to a significant amount of carbon dioxide formation. There would be a significant benefit in a process that could produce olefins (and ultimately, a synthetic fossil fuel) from alcohols with a higher carbon efficiency and at the same or lower cost than known in the art.

SUMMARY OF THE INVENTION

The present disclosure is directed to catalysts useful in the conversion of alcohols to olefins, as well as methods for the conversion of alcohols to olefins by use of these catalysts. The catalysts described herein have been found to produce olefins from alcohols with high carbon efficiency and at the same or lower cost than conventional methods. In a first embodiment, the catalyst includes the following components: (a) beta zeolite; (b) at least one element selected from zinc, magnesium, calcium, strontium, sodium, and potassium; and (c) at least one element selected from hafnium, yttrium, zirconium, tantalum, niobium, and tin; wherein the components (b) and (c) are independently within the beta zeolite or on a surface of the beta zeolite. In some embodiments, the catalyst further includes component (d), which is copper or silver. In further embodiments, the catalyst described above (i.e., the "first catalyst") is in admixture with a second catalyst capable of converting alcohols to olefins, wherein the second catalyst contains metal oxide particles having on their surfaces copper and at least one element selected from platinum, palladium, and nickel, and wherein the metal oxide is selected from at least one of aluminum oxide, zirconium oxide, cerium oxide, titanium oxide, silicon oxide (silica), and zinc oxide. In the method, one or more alcohols are contacted with any of the above-described catalysts at a temperature of at least 100° C. and up to 500° C. to result in the one or more alcohols being converted to one or more olefinic compounds. The olefinic compounds may be alkenes (e.g., butenes) and/or 1,3-butadiene.

In the process, ethanol is converted to higher olefins, e.g., butenes, which can be readily converted to jet fuel or other synthetic fossil fuel with high carbon efficiency and low oligomerization cost. Moreover, the reactions proceed with negligible $CO_2$ formation. The catalysts described herein can also handle high space velocity and alcohol (e.g., ethanol) concentration, which permits a significant reduction in the reactor size and operational cost. Meanwhile, the process is also amenable for selectively producing 1,3-butadiene, which is a high value chemical commodity since it is used as a precursor for a number of applications, including in the production of rubber and plastics.

The present disclosure is directed to new catalyst materials for converting either pure alcohols or aqueous solutions thereof into jet fuel and valuable co-products (e.g., 1,3-butadiene). In particular embodiments, the catalyst converts ethanol to butene-rich olefins in the presence of hydrogen (i.e., hydrogen gas). Ethylene, propene, and $C_5$-$C_7$ olefins are generally also produced. These olefins can then be oligomerized and hydrogenated into jet fuel. Based on one of the catalysts studied herein, Cu—Hf—Zn/BEA, approximately 96% of $C_2$-$C_8$ olefins can be produced, with about 68% of the olefins being $C_3^+$ olefins. The yield of $C_3^+$ olefins may reach ~90% after additional process optimization. Notably, the $C_3^+$ olefins can be readily converted to synthetic jet fuel. The present disclosure also describes some other new types of catalysts, including a physical mixture of Cu—Hf—Zn/BEA with Pt—Cu/$Al_2O_3$, and a physical mixture of Zn—Y/BEA with Pt—Cu/$Al_2O_3$. Notably, hydrogen is not needed in the catalytic process when using the physical mixture, and thus, hydrogen can be not present (i.e., absent) in the catalytic conversion process when using the physical mixture. Using the catalyst Cu—Hf—Zn/BEA, ethanol can be converted to 1,3-butadiene when the carrier gas is changed to nitrogen. Olefin mixtures (e.g., ethylene, propene, butenes and $C_5$-$C_7$ olefins) are produced as side products, and these can be separated and combined with one or more other olefin streams for downstream oligomerization and hydrogenation reactions to produce jet fuel.

DETAILED DESCRIPTION OF THE INVENTION

In the conversion method described herein, an alcohol is catalytically converted to one or more olefinic compounds (i.e., one or more "olefins") by contacting the alcohol with a metal-loaded zeolite catalyst at a suitable temperature (e.g., at least 100° C. and up to 500° C.) to result in the alcohol being converted to the one or more olefins. As used herein, the term "alcohol" is meant to include a single alcohol or a mixture of two or more alcohols. The term "olefinic compounds" (i.e., "olefins") refers primarily to alkenes (e.g., $C_3$-$C_8$), which includes mono-enes and dienes 1,3-butadiene).

The alcohol considered herein is generally of the formula R—OH, where R is typically a straight-chained or branched alkyl group having at least one or two carbon atoms and up to any number of carbon atoms, e.g., up to 3, 4, 5, or 6 carbon atoms, but more typically, up to three or four carbon atoms. The alcohol is typically a primary or secondary alcohol. Some examples of suitable alcohols include methanol, ethanol, n-propanol, isopropanol, n-butanol, isobutanol, sec-butanol, tert-butanol, n-pentanol, and isopentanol. In some embodiments, the alcohol starting material contains at least ethanol, or ethanol in combination with one or more of the alcohols provided above, or an absence of any one or more alcohols other than ethanol, such as an absence of any one or more of the alcohols provided above other than ethanol.

The alcohol can be in any concentration, including pure (dry) alcohol, i.e., at or about 100% or in aqueous solution. In some embodiments, the alcohol considered herein, to be converted to olefins, is one that can be produced by a fermentation process (i.e., a bio-alcohol). Most notable examples of bio-alcohols considered herein include ethanol, n-butanol (i.e., butanol), and isobutanol. In different embodiments, the alcohol can be ethanol, or butanol, or isobutanol, or a combination thereof, as commonly found in fermentation streams. In particular embodiments, the alcohol is an aqueous solution of alcohol (i.e., the alcohol is a component of an aqueous solution), such as found in fermentation streams. In fermentation streams, the alcohol is typically in a concentration of no more than about 20% (vol/vol), 15%, 10%, or 5%, wherein the term "about" generally indicates within ±0.5%, 1%, 2%, 5%, or up to ±10% of the indicated value. The aqueous solution of alcohol may contain the alcohol in any of the foregoing amounts. In some embodiments, a fermentation stream or other alcoholic aqueous solution is directly contacted with the catalyst (typically, after filtration to remove solids) to effect the conversion of the alcohol in the fermentation stream. In other embodiments, the fermentation stream or other alcoholic aqueous solution is concentrated in alcohol (for example, of at least or up to 20%, 30%, 40%, or 50%) before contacting the fermentation stream with the catalyst. In yet other embodiments, alcohol in the fermentation stream or other alcoholic aqueous solution is selectively removed from the alcoholic aqueous solution, such as by distillation, to produce a substantially pure form of alcohol as the feedstock (e.g., a concentration of at least 90% or 95% of alcohol). In still other embodiments, the alcohol is completely dewatered into 100% alcohol before contacting with the catalyst.

The olefinic compounds herein produced by the catalytic conversion of alcohols generally include a range of alkenes (e.g., ethylene, propene, butenes, and $C_5$-$C_7$ alkenes) and/or dienes (e.g., 1,3-butadiene, 1,3-hexadiene, or 1,5-hexadiene). The term "alkenes," as used herein, refers to hydrocarbon compounds containing a single carbon-carbon double bond, as opposed to 1,3-butadiene, which contains two carbon-carbon double bonds. Some examples of $C_4^+$ alkenes include 1-butene, 2-butene, 1-pentene, cis-2-pentene, trans-2-pentene, isopentene 3-methyl-1-butene), 1-hexene, cis-2-hexene, trans-2-hexene, cis-3-hexene, trans-3-hexene, isohexene (4-methyl-1-pentene), 3-methyl-1-pentene, 3,4-dimethyl-1-pentene, 1-heptene, isoheptene (5-methyl-1-hexene), 4-methyl-1-hexene, and 1-octene, 2,4,4-trimethyl-1-pentene.

In the process, a suitable reaction temperature is employed during contact of the of the one or more alcohols with the catalyst. Generally, the reaction temperature is at least 100° C. and up to 500° C. In different embodiments, the reaction temperature is precisely or about, for example, 100° C., 125° C., 150° C., 175° C., 200° C., 225° C., 250° C., 275° C., 300° C., 325° C., 350° C., 375° C., 400° C., 425° C., 450° C., 475° C., or 500° C., or a temperature within a range bounded by any two of the foregoing exemplary temperatures, e.g., 100° C.-500° C., 200° C.-500° C., 300° C.-500° C., 350° C.-500° C., 400° C.-500° C., 100° C.-450° C., 200° C.-450° C., 250° C.-450° C., 300° C.-450° C., 100° C.-400° C., 200° C.-400° C., 300° C.-400° C., 100° C.-300° C., or 200° C.-300° C. Generally, ambient (i.e., normal atmospheric) pressure of about 1 atm is used in the method described herein. However, in some embodiments, an elevated pressure may be used. For example, in some embodiments, the pressure may be elevated to, for example, 1.5, 2, 3, 4, or 5 atm.

The catalyst herein used for converting an alcohol to olefinic compounds contains a beta zeolite (i.e., BEA) structure that includes certain catalytically active metals (in the cationic state) within and/or on a surface of the BEA structure. The BEA structure is herein referred to as "component (a)". More specifically, the beta zeolite includes at least one element selected from zinc, magnesium, calcium, strontium, sodium, and potassium (herein referred to collectively as "component (b)"), and at least one element selected from hafnium, yttrium, zirconium, tantalum, niobium, and tin (herein referred to as "component (c)"), wherein the components (b) and (c) are independently within or on a surface of the beta zeolite. The foregoing catalyst is herein referred to as the "first catalyst". The total amount of any one or more of the foregoing active metals that are present in the catalyst may be, for example, 0.1, 0.2, 0.5, 1, 2, 5, 10, 15, 20, 25, or 30 wt %, or in an amount within a range bounded by any two of the foregoing amounts. The BEA structure may also possess any suitable silica-to-alumina (i.e., $SiO_2/Al_2O_3$ or "Si/Al") ratio. For example, the zeolite can have a Si/Al ratio of precisely, at least, more than, less than, or up to 4, 5, 6, 7, 8, 9, 10, 11, 12, 13, 14, 15, 20, 25, 30, 35, 40, 45, 50, 55, 60, 65, 70, 75, 80, 85, 90, 95, 100, 120, 150, or 200, or a Si/Al ratio within a range bounded by any two of the foregoing values. Beta zeolite compositions having a Si/Al ratio of at least or greater than 10, 20, 50, 100, 200, or 500 are herein considered as dealuminated beta zeolites. Notably, in some embodiments, a pure silicon (no Al) beta zeolite may be used. In some embodiments, the zeolite may also be a pillared zeolite.

Various possible embodiments for the first catalyst are provided as follows. In a first set of embodiments, the beta zeolite includes zinc in combination with one or more elements of component (c). In a second set of embodiments, the beta zeolite includes magnesium in combination with one or more elements of component (c). In a third set of embodiments, the beta zeolite includes calcium in combination with one or more elements of component (c). In a fourth set of embodiments, the beta zeolite includes strontium in combination with one or more elements of component (c). In a fifth set of embodiments, the beta zeolite includes sodium in combination with one or more elements of component (c). In a sixth set of embodiments, the beta zeolite includes potassium in combination with one or more elements of component (c). In a seventh set of embodiments, the beta zeolite includes hafnium in combination with one or more elements of component (b). In an eighth set of embodiments, the beta zeolite includes yttrium in combination with one or more elements of component (b). In a ninth set of embodiments, the beta zeolite includes zirconium in combination with one or more elements of component (b). In a tenth set of embodiments, the beta zeolite includes tantalum in combination with one or more elements of component (b). In an eleventh set of embodiments, the beta zeolite includes niobium in combination with one or more elements of component (b). In a twelfth set of embodiments, the beta zeolite includes tin in combination with one or more elements of component (b). In some embodiments, the beta zeolite includes at least zinc and either or both of hafnium or yttrium. In other embodiments, one or more metals from component (b) or component (c) are excluded from the catalyst.

The beta zeolite (first) catalyst may also include copper or silver within or on a surface of the beta zeolite. The copper or silver is herein referred to as "component (d)". The copper or silver may be included in any of the above exemplary zeolite embodiments enumerated above for combinations of components (b) and (c). In particular embodiments, the beta zeolite includes at least copper, zinc, and either or both of hafnium or yttrium, or the beta zeolite includes at least silver, zinc, and either or both of hafnium or yttrium.

Compositions pertaining to the first catalyst, as described above, can be synthesized by methods well known in the art. The method may incorporate the metal ions homogeneously into the zeolite or as a coating (e.g., as nanoparticles) on surfaces of the zeolite. In particular embodiments, the catalyst described herein is prepared by a solid-state ion exchange method in which the zeolite is physically mixed (e.g., by grinding) with one or more metal nitrate precursors, followed by calcining (e.g., at a temperature of 500-600° C.) for a suitable period of time (e.g., 1-12 hours). For purposes of the present invention, the zeolite being impregnated with nitrate precursors is typically a dealuminated zeolite. In other embodiments, the catalyst can be prepared by, first, treating the zeolite (which may or may not be dealuminated) with one or more solutions containing salts of the metals to be loaded. The metal-containing solution may be contacted with the zeolite such that the solution is absorbed into the zeolite, preferably into the entire volume of the zeolite. In one embodiment, the impregnating step is achieved by treating the zeolite with a solution that contains all of the metals to be loaded. In another embodiment, the impregnating step is achieved by treating the zeolite with two or more solutions, wherein the different solutions contain different metals or combinations of metals. Each treatment of the zeolite with an impregnating solution corresponds to a separate impregnating step. Typically, when more than one impregnating step is employed, a drying and/or thermal treatment step is employed between the impregnating steps. The preparation of a number of types of zeolites, including pillared forms of two-dimensional zeolites, is described in, for example, W. J. Roth et al., *Chem. Rev.*, 114, 4807-4837, 2014, the contents of which are herein incorporated by reference.

In some embodiments, the first catalyst described above is used in combination with a second catalyst also capable of converting the alcohol to olefins or that augments the ability of the first catalyst to convert the alcohol to olefins. The second catalyst contains metal oxide particles having on their surfaces copper and at least one element selected from platinum, palladium, and nickel, wherein the metals may independently be present in their metallic (zerovalent) or cationic states. The metal oxide is selected from aluminum oxide, zirconium oxide, cerium oxide, titanium oxide, silicon oxide, and zinc oxide. In a first embodiment, the first catalyst is in admixture with the second catalyst during the conversion process of the alcohol. In a second embodiment, a two-stage process is employed in which the alcohol is first reacted with the first catalyst to produce intermediate products that are then reacted with the second catalyst.

In a first set of embodiments, the second catalyst contains copper and platinum on surfaces of particles having an aluminum oxide, zirconium oxide, cerium oxide, titanium oxide, silicon oxide, or zinc oxide composition. In a second set of embodiments, the second catalyst contains copper and palladium on surfaces of particles having an aluminum oxide, zirconium oxide, cerium oxide, titanium oxide, silicon oxide, or zinc oxide composition. In a third set of embodiments, the second catalyst contains copper and nickel on surfaces of particles having an aluminum oxide, zirconium oxide, cerium oxide, titanium oxide, silicon oxide, or zinc oxide composition. The total amount of any one or more of the foregoing active metals that are present in the catalyst may be, for example, 0.1, 0.2, 0.5, 1, 2, 5, 10, 15, 20, 25, or 30 wt %, or in an amount within a range bounded by any two of the foregoing amounts. The particles are typically nanoparticles, which typically have a size of up to or less than 1000 nm, and more typically, at least 1, 2, or 5 nm and up to 10, 15, 20, 30, 40, 50, 100, 200, or 500 nm.

Compositions pertaining to the second catalyst, as described above, can be synthesized by methods well known in the art. Metal oxide nanoparticles can be produced by a number of sol-gel and hydrothermal methods well known in the art, e.g., H. S. Lim, et al., *AIP Conference Proceedings*, 1571, 812 (2013) and S. Sagadevan et al., *Journal of Materials Science: Materials in Electronics*, 27(6), 5622-5627, June 2016, the contents of which are herein incorporated by reference. Metals, such as Pt and Cu, can be deposited on or within such metal oxide nanoparticles by means well known in the art, such described in, e.g., T. Epron et al., *Journal of Catalysis*, 198(2), 309-318; Mar. 10, 2001; and Z. Han et al., *Nanoscale*, 6(17), 10000-8, September 2014; and L. E. Gomez et al., *International Journal of Hydrogen Energy*, 39(8), 3719-3729, March 2014, the contents of which are collectively herein incorporated by reference.

In a first set of embodiments, the first catalyst contains component (d), i.e., copper and/or silver, and the first catalyst may or may not be used in combination with the second catalyst. The foregoing catalyst is particularly useful in converting an alcohol to alkenes in greater yield than 1,3-butadiene. In a second set of embodiments, the first catalyst does not contain component (d), i.e., copper and/or silver, and the first catalyst is used in combination with the second catalyst. The foregoing catalyst is also particularly useful in converting an alcohol to alkenes in greater yield than 1,3-butadiene. In a third set of embodiments, the first catalyst does not contain component (d), i.e., copper or silver, and the first catalyst is also not used in combination with the second catalyst. The foregoing embodiment is particularly useful in converting an alcohol to 1,3-butadiene in greater yield than alkenes. Notably, the conversion of alcohol to olefins is typically conducted under a hydrogen atmosphere when the first catalyst with or without component (d) and without the second catalyst is used; in contrast, the conversion of alcohol to olefins may be conducted under a hydrogen or non-hydrogen (e.g., inert gas, such as nitrogen) atmosphere when the first catalyst, with or without component (d), is used in combination with the second catalyst.

In some embodiments, by appropriate choice of the catalyst and process conditions (e.g., temperature), the method produces predominantly one type of product, wherein the term "predominantly" generally corresponds to a yield of greater than 50%, although, in some cases, a yield of at least 40%, 45%, or 50% may correspond to a predominant amount. For example, in some embodiments, $C_2$-$C_8$ mixed alkenes or sub-group therein (particularly $C_4$ alkenes, i.e., butenes) are produced in at least or greater than 40%, 45%, or 50% yield; or 1,3-butadiene is produced in at least or greater than 40%, 45%, or 50% yield. In some embodiments, the yield for any of the foregoing compounds may be at least or greater than, for example, 55%, 60%, 65%, 70%, 75%, 80%, 85%, or 90%.

The catalyst and reactor can have any of the designs known in the art for catalytically treating a fluid or gas at elevated temperatures, such as a fluidized bed reactor. The process may be in a continuous or batch mode. In particular embodiments, the alcohol is injected into a heated reactor such that the alcohol is quickly volatilized into gas, and the gas passed over the catalyst. In some embodiments, the reactor design includes a boiler unit and a reactor unit if the fermentation stream is used directly as a feedstock without purification. The boiler unit is generally not needed if the fermentation stream is distilled to concentrate ethanol because the distillation process removes the dissolved solids in the fermentation streams. The boiler unit volatilizes liquid feedstock into gases prior to entry into the reactor unit and withholds dissolved solids.

In the method, additional catalysts can be employed to convert initial olefinic compounds produced by the above-described catalyst(s) to a synthetic fossil fuel (e.g., jet fuel), fuel additive, or commodity chemical. The term "synthetic fossil fuel" refers to a mixture of hydrocarbon compounds useful as a fuel or as a blendstock in a fuel. The mixture of hydrocarbon compounds produced herein substantially corresponds (e.g., in composition and/or properties) to a known petrochemical fuel, such as petroleum, or a fractional distillate of petroleum. Some examples of petrochemical fuels include jet fuel jet propellant, such as JP-8), gasoline, kerosene, and diesel. Like hydrocarbon fuel grades in current use, the mixture of hydrocarbon compounds produced herein can, in some embodiments, be predominantly or exclusively composed of alkanes, alkenes, aromatics, or a mixture thereof. Although aromatics (particularly benzene) may be present in the hydrocarbon mixture, their presence may be minimized to adhere to current fuel standards. The raw hydrocarbon product may also be fractionated by distillation into different fuel grades, each of which is known to be within a certain boiling point range. A particular advantage of the instant method is its ability to produce such fuel grades in the substantial absence of contaminants (e.g., mercaptans) normally required to be removed during the petroleum refining process. Moreover, by appropriate adjustment of the catalyst and processing conditions, a select distribution of hydrocarbons can be obtained.

To effect the further conversion, the olefinic compounds are reacted with one or more additional ("third") catalysts known in the art capable of such transformation. The additional catalyst may be, for example, a zeolite (e.g., H-BEA, MCM, H-ZSM-22, or H-ZSM-57), amorphous aluminosilicate, sulfonic acid ion-exchange resin (e.g., Amberlyst® 15, Amberlyst® 35, Amberlyst® 36, Purolite®, Dowex®, Lewatit®), or solid phosphoric acid. The conditions of the reaction may be, for example, 100-500° C. (or more particularly, 70-350° C.), 1-60 atm, a weight hourly space velocity (WHSV) of 0.1 hr$^{-1}$ to 20 h$^{-1}$, and an inert or hydrogen carrier gas. The foregoing catalysts and conditions are generally suited for a dimerization, oligomerization, or dehydrocyclization process. However, the process may also include a hydrogenation process, which may employ an oxide catalyst (e.g., $Al_2O_3$, $TiO_2$, $CeO_2$, or $ZrO_2$) coated or impregnated with platinum (Pt), nickel (Ni), rhodium (Rh), ruthenium (Ru) or other noble metal or precious metal. In some embodiments, zinc (Zn) or phosphorus (P) is included in the zeolite (e.g., ZSM-5) to make the catalyst more selective for converting butenes to one or more of benzene, toluene, and xylenes (particularly p-xylene). In some embodiments, the oligomerization and hydrogenation occur simultaneously, while in other embodiments, the oligomerization and hydrogenation occur in separate steps.

Any of the catalysts described above can also be mixed with or affixed onto a support material suitable for the conditions of the conversion reaction. The support material can be a powder (e.g., having any of the above particle sizes), granular (e.g., 0.5 mm or greater particle size), a bulk material, such as a honeycomb monolith of the flow-through type, a plate or multi-plate structure, or corrugated metal sheets. If a honeycomb structure is used, the honeycomb structure can contain any suitable density of cells. For example, the honeycomb structure can have 100, 200, 300, 400, 500, 600, 700, 800, or 900 cells per square inch (cells/in$^2$) (or from 62-140 cells/cm$^2$) or greater. The support material is generally constructed of a refractory composition, such as those containing cordierite, mullite, alumina (e.g., α-, β-, or γ-alumina), or zirconia, or a combination thereof. Honeycomb structures, in particular, are described in detail in, for example, U.S. Pat. Nos. 5,314,665, 7,442, 425, and 7,438,868, the contents of which are incorporated herein by reference in their entirety. When corrugated or other types of metal sheets are used, these can be layered on top of each other with catalyst material supported on the sheets such that passages remain that permit the flow of the liquid or gas containing the organic species undergoing conversion. The layered sheets can also be formed into a structure, such as a cylinder, by winding the sheets.

Depending on the final composition of the hydrocarbon product, the product can be directed to a variety of applications, including, for example, as precursors for plastics, polymers, and fine chemicals. The process described herein can advantageously produce a range of hydrocarbon products that differ in any of a variety of characteristics, such as molecular weight (i.e., hydrocarbon weight distribution), degree of saturation or unsaturation (e.g., alkane to alkene ratio), and level of branched or cyclic isomers. The process provides this level of versatility by appropriate selection of, for example, composition of the catalyst (e.g., catalytic metal), amount of catalyst (e.g., ratio of catalyst to alcohol precursor), processing temperature, and flow rate (e.g., LHSV).

In some embodiments, the conversion method described above is integrated with a fermentation process, wherein the fermentation process produces the alcohol used as feedstock for the conversion process. By being "integrated" is meant that alcohol produced at a fermentation facility or zone is sent to and processed at a conversion facility or zone that performs the conversion process described above. Preferably, in order to minimize production costs, the fermentation process is in close enough proximity to the conversion facility or zone, or includes appropriate conduits for transferring produced alcohol to the conversion facility or zone, thereby not requiring the alcohol to be shipped. In particular embodiments, the fermentation stream produced in the fermentation facility is directly transferred to the conversion facility, generally with removal of solids from the raw stream (generally by filtration or settling) before contact of the stream with the catalyst.

In some embodiments, the fermentation process is performed in an autonomous fermentation facility, i.e., where saccharides, produced elsewhere, are loaded into the fermentation facility to produce alcohol. In other embodiments, the fermentation process is part of a larger biomass reactor facility, i.e., where biomass is decomposed into fermentable saccharides, which are then processed in a fermentation zone. Biomass reactors and fermentation facilities are well known in the art. Biomass generally refers to lignocellulosic matter (i.e., plant material), such as wood, grass, leaves, paper, corn husks, sugar cane, bagasse, and nut hulls. Generally, biomass-to-ethanol conversion is performed by 1) pretreating biomass under well-known conditions to loosen lignin and hemicellulosic material from cellulosic material, 2) breaking down cellulosic material into fermentable saccharide material by the action of a cellulose enzyme, and 3) fermentation of the saccharide material, typically by the action of a fermenting organism, such as suitable yeast, to produce one or more alcohols.

In other embodiments, the alcohol is produced from a more direct sugar source, such as a plant-based source of sugars, such as sugar cane or a grain starch (such as corn starch). Ethanol production via corn starch (i.e., corn starch ethanol) and via sugar cane (i.e., cane sugar ethanol) currently represent some of the largest commercial production methods of ethanol. Integration of the instant conversion process with any of these large scale ethanol production methods is contemplated herein.

Examples have been set forth below for the purpose of illustration and to describe certain specific embodiments of the invention. However, the scope of this invention is not to be in any way limited by the examples set forth herein.

Example 1

Cu—Y—Zn/BEA Catalyst for Ethanol Conversion to Olefins

Dealumination of H-BEA Zeolite. H-BEA (SAR=11.5) was mixed with 250 mL nitric acid (69% to 70%) and heated to 80° C. with 500 rpm stirring for 12 hours. The dealuminated BEA was centrifuged and washed with DI water until the pH was close to 9. The washed powder was dried under 90° C. in an oven overnight followed by calcination to 550° C. (1° C./min ramping rate) for 6 hours to remove moisture and nitric acid in the framework. The sample was labeled as DeAlBEA as the support for metal loading.

Loading of Zn, Y and Cu. The loading amount of metal was calculated based on the weight percent of pure metal compared with zeolite support. Copper nitrate trihydrate, zinc nitrate hexahydrate and yttrium nitrate hexahydrate were mixed with DeAlBEA zeolite support in the mortar and ground for 20 minutes. The mixed powder was a homogeneous light green without any obvious white or blue particles. The product was calcined to 550° C. at a 1° C./min ramping rate and held for 6 hours to provide a homogeneous distribution of metals in the zeolite framework.

Catalytic Test. The reaction was carried out in a tubular fixed-bed quartz reactor in a vertical tubular furnace. Typically, 0.15 g catalysts were treated in situ by heating at 5 K min$^{-1}$ to 673 K and holding at 673 K under He flow (15 ccm) for 15 minutes to remove adsorbed species before measuring catalytic performance. Flow rates of He and $H_2$ were set using mass flow controllers. Ethanol was ted by syringe pumps and was evaporated inside the ⅛-inch stainless steel transfer lines. The types and concentrations of reactants and products in the stream were measured by a gas-chromatograph with thermal conductivity detector (T(D) and a flame ionization detector (FID). A gas chromatograph mass-spectrometer (GC-MS) was used to determine the peak position of reactants and products. The results are summarized in Table 1 below.

TABLE 1

| Catalyst Performance of Cu—Y—Zn/BEA | | | | | | | | | | |
|---|---|---|---|---|---|---|---|---|---|---|
| Zeolite | Temp (K) | WHSV (h$^{-1}$) | Conversion (%) | Ethylene Yield (%) | Propene Yield (%) | Butadiene Yield (%) | Butene Yield (%) | $C_{4+}$ Olefin Yield (%) | Total Olefin Yield (%) | $C_1$ to $C_3$ Paraffin Yield (%) |
| $Cu_{1.0}Y_{8.0}Zn_{2.0}$/BEA$^a$ | 603 | 0.31 | 94.77 | 10.48 | 5.99 | 0.54 | 66.02 | 5.12 | 88.16 | 0.32 |
| $Cu_{1.0}Y_{8.0}Zn_{2.0}$/BEA$^a$ | 627 | 0.31 | 100.00 | 15.24 | 7.82 | 2.40 | 66.79 | 3.90 | 96.16 | 0.33 |
| $Cu_{1.0}Y_{8.0}Zn_{2.0}$/BEA$^a$ | 651 | 0.31 | 100.00 | 19.96 | 11.23 | 0.29 | 59.14 | 5.51 | 96.14 | 0.64 |
| $Cu_{1.0}Y_{8.0}Zn_{2.0}$/BEA$^a$ | 674 | 0.31 | 100.00 | 21.35 | 10.45 | 0.98 | 56.62 | 7.33 | 96.73 | 0.94 |
| $Cu_{1.0}Y_{8.0}Zn_{2.0}$/BEA$^b$ | 599 | 0.32 | 100.00 | 7.96 | 7.71 | 56.98 | 14.00 | 8.88 | 95.52 | 0.13 |
| $Cu_{1.0}Y_{8.0}Zn_{2.0}$/BEA$^b$ | 624 | 0.32 | 100.00 | 10.73 | 9.35 | 50.24 | 14.68 | 9.15 | 94.14 | 0.20 |
| $Cu_{1.0}Y_{8.0}Zn_{2.0}$/BEA$^b$ | 647 | 0.32 | 100.00 | 12.75 | 10.90 | 44.57 | 14.62 | 11.05 | 93.90 | 0.33 |
| $Cu_{1.0}Y_{8.0}Zn_{2.0}$/BEA$^b$ | 670 | 0.32 | 100.00 | 15.89 | 13.55 | 35.04 | 15.31 | 13.65 | 93.44 | 0.68 |

$^a$$H_2$ was applied as carrier gas.
$^b$He was applied as carrier gas

Example 2

Physical Mixture of Zn—Y/BEA and Pt0.1Cu10/$Al_2O_3$ Single Atom Catalyst for Ethanol Conversion to Olefins Preparation of Pt0.1Cu10/$Al_2O_3$ Single Atom Catalyst. The catalyst was prepared by an incipient wetness impregnation method. $H_2PtCl_6\cdot 6$ $H_2O$ and $Cu(NO_3)_2\cdot 3$ $H_2O$ were used as precursors and γ-$Al_2O_3$ was used as support. After impregnation, the catalysts were placed statically overnight and dried at 100° C. for 12 hours and then calcined at 600° C. for 2 hours. The catalyst was found to have 0.1 wt % Pt and 10 wt % Cu.

Preparation of Zn-Y/BEA. The loading amount of metal was calculated based on the weight percent of pure metal compared with zeolite support. Zinc nitrate hexahydrate and yttrium nitrate hexahydrate were mixed with DeAlBEA zeolite support in the mortar and ground for 20 minutes. The mixed powder was a homogeneous light green without any obvious white or blue particles. The product was calcined to 550° C. at a 1° C./min ramping rate and held for 6 hours to provide a homogeneous distribution of metals in the zeolite framework.

The results are summarized in Table 2 below.

TABLE 2

Catalytic Performance for the Mixed Zn-Y/BEA-0.1Pt10Cu/Al$_2$O$_3$ Catalyst

| Zeolite | Temp (C.) | WHSV (h$^{-1}$) | Conversion (%) | Ethylene Yield (%) | Propene Yield (%) | Butadiene Yield (%) | Butene Yield (%) | C$_2$ to C$_8$ Olefin Yield (%) |
|---|---|---|---|---|---|---|---|---|
| Zn2Y8/BEA + Pt0.1Cu10/Al$_2$O$_3$ (3:2, weight ratio)$^a$ | 309 | 0.38 | 97 | 4.56 | 5.34 | 2.33 | 61.30 | 77.99 |
| Zn2Y8/BEA + Pt0.1Cu10/Al$_2$O$_3$ (3:2)$^b$ | 325 | 0.19 | 100 | 3.90 | 5.20 | 0.60 | 69.00 | 84.90 |
| Zn2Y8/BEA + Pt0.1Cu10/Al$_2$O$_3$ (3:2)$^c$ | 350 | 1.02 | 92 | 4.88 | 5.61 | 1.66 | 56.95 | 76.08 |
| Zn2Y8/BEA + Pt0.1Cu10/Al$_2$O$_3$ (3:2)$^d$ | 350 | 0.76 | 98 | 5.47 | 6.25 | 0.68 | 65.17 | 83.92 |

$^a$Pure He carrier gas;
$^{b,c,d}$He + 2 ccm H$_2$ as carrier gas

Example 3

Cu—Hf—Zn/BEA Catalyst for Ethanol Conversion to Olefins

Dealumination of H-BEA Zeolite. H-BEA (SAR=11.5) was mixed with 250 mL nitric acid (69% to 70%) and heated to 80° C. with 500 rpm stirring for 12 hours. The dealuminated BEA was centrifuged and washed with DI water until the pH was close to 9. The washed powder was dried under 90° C. in an oven overnight followed by calcination to 550° C. (1° C./min ramping rate) for 6 hours to remove moisture and nitric acid in the framework. The sample was labeled as DeAlBEA as the support for metal loading.

Loading of Zn, Hf and Cu. The loading amount of metal was calculated based on the weight percent of pure metal compared with zeolite support. Copper nitrate trihydrate, zinc nitrate hexahydrate and hafnium oxychloride were dissolved in water and loaded onto the support using an impregnation method. The product was calcinated to 550° C. at a 1° C./min ramping rate and held for 6 hours to provide a homogeneous distribution of metals in the zeolite framework.

Catalytic Test. The reaction was carried out in a tubular fixed-bed quartz reactor in a vertical tubular furnace. Typically, 0.15 g catalysts were treated in situ by heating at 5 K min$^{-1}$ to 673 K and holding at 673 K under He flow (15 ccm) for 15 minutes to remove adsorbed species before measuring catalytic performance. Flow rates of He and H$_2$ were set using mass flow controllers. Ethanol was fed by syringe pumps and was evaporated inside the ⅛-inch stainless steel transfer lines. The types and concentrations of reactants and products in the stream were measured by a gas-chromatograph with a thermal conductivity detector (TCD) and flame ionization detector (FID). A gas chromatograph mass-spectrometer (GC-MS) was used to determine the peak position of reactants and products. The results are summarized in Table 3 below.

TABLE 3

Catalyst performance of Cu—Hf—Zn/BEA

| Temp. (K) | WHSV (h$^{-1}$) | Ethanol Concentration (%) | Conversion | Ethylene Sel$^c$ (%) | Propene Sel (%) | Butenes Sel (%) | Butadiene Sel (%) | C5+ olefins Sel (%) | Oxygenate Sel (%) | Paraffin Sel (%) |
|---|---|---|---|---|---|---|---|---|---|---|
| 330$^a$ | 0.32 | 2.4% | 100 | 21.2 | 5.5 | 15.2 | 50.4 | 0 | 7.8 | 0 |
| 330$^a$ | 0.63 | 2.4% | 100 | 15.3 | 3.8 | 17.1 | 47.0 | 0 | 16.7 | 0 |
| 350$^a$ | 0.63 | 2.4% | 100 | 19.5 | 5.3 | 14.3 | 51.2 | 0.3 | 9.4 | 0 |
| 350$^b$ | 0.63 | 6.9% | 87 | 29.8 | 0 | 37.2 | 10.8 | 1.0 | 16.9 | 4.3 |

$^a$under pure He condition.
$^b$under hydrogen environment.
$^c$"Sel" = Selectivity While there have been shown and described what are at present considered the preferred embodiments of the invention, those skilled in the art may make various changes and modifications which remain within the scope of the invention defined by the appended claims.

What is claimed is:

1. A catalyst composition for converting an alcohol to olefins, the catalyst composition comprising the following components:
    (a) beta zeolite;
    (b) at least one element selected from the group consisting of zinc, magnesium, calcium, strontium, sodium, and potassium; and
    (c) at least one element selected from the group consisting of hafnium, yttrium, zirconium, tantalum, niobium, and tin;
    wherein the components (b) and (c) are independently within said beta zeolite or on a surface of said beta zeolite.

2. The catalyst composition of claim 1, further comprising component (d), which is copper or silver.

3. The catalyst composition of claim 1, wherein said beta zeolite has a silicon to aluminum ratio of at least 10.

4. The catalyst composition of claim 1, wherein said component (b) comprises zinc.

5. The catalyst composition of claim 1, wherein said component (c) comprises hafnium or yttrium.

6. The catalyst composition of claim 1, wherein said component (b) comprises zinc and said component (c) comprises hafnium or yttrium.

7. The catalyst composition of claim 2, wherein at least one of said copper or silver is on a surface of said beta zeolite.

8. The catalyst composition of claim 7, wherein zinc and at least one of said copper or silver are on a surface of said beta zeolite.

9. The catalyst composition of claim 1, wherein the catalyst composition includes copper, hafnium, and zinc independently within said beta zeolite or on a surface of said beta zeolite.

10. The catalyst composition of claim 1, wherein said catalyst is in admixture with a second catalyst capable of converting said alcohol to olefins, the second catalyst comprising metal oxide particles having on their surfaces copper and at least one element selected from the group consisting of platinum, palladium, and nickel, and wherein said metal oxide is selected from the group consisting of aluminum oxide, zirconium oxide, cerium oxide, titanium oxide, silicon oxide, and zinc oxide.

11. A method for converting an alcohol to one or more olefinic compounds, the method comprising contacting the alcohol with a catalyst at a temperature of at least 100° C. and up to 500° C. to result in said alcohol being converted to said one or more olefinic compounds, wherein said catalyst comprises the following components:
(a) beta zeolite;
(b) at least one element selected from the group consisting of zinc, magnesium, calcium, strontium, sodium, and potassium; and
(c) at least one element selected from the group consisting of hafnium, yttrium, zirconium, tantalum, niobium, and tin;
wherein the components (b) and (c) are independently within said beta zeolite or on a surface of said beta zeolite.

12. The method of claim 11, wherein said alcohol has one to four carbon atoms.

13. The method of claim 11, wherein said alcohol is ethanol.

14. The method of claim 11, wherein said olefinic compounds are comprised of butenes and 1,3-butadiene.

15. The method of claim 14, wherein said olefinic compounds include butenes produced in at least 40% yield.

16. The method of claim 14, wherein said olefinic compounds include 1,3-butadiene produced in at least 40% yield.

17. The method of claim 11, wherein said catalyst further comprises component (d), which is copper or silver.

18. The method of claim 11, wherein said beta zeolite has a silicon to aluminum ratio of at least 10.

19. The method of claim 11, wherein said component (b) comprises zinc.

20. The method of claim 11, wherein said component (c) comprises hafnium or yttrium.

21. The method of claim 11, wherein said component (b) comprises zinc and said component (c) comprises hafnium or yttrium.

22. The method of claim 17, wherein at least one of said copper or silver is on a surface of said beta zeolite.

23. The method of claim 22, wherein zinc and at least one of said copper or silver are on a surface of said beta zeolite.

24. The method of claim 11, wherein the catalyst composition includes copper, hafnium, and zinc independently within said beta zeolite or on a surface of said beta zeolite.

25. The method of claim 11, wherein said catalyst is in admixture with a second catalyst capable of converting said alcohol to said one or more olefinic compounds, the second catalyst comprising metal oxide particles having on their surfaces copper and at least one element selected from the group consisting of platinum, palladium, and nickel, and wherein said metal oxide is selected from the group consisting of aluminum oxide, zirconium oxide, cerium oxide, titanium oxide, silicon oxide, and zinc oxide.

26. The method of claim 25, wherein the method converts the alcohol to said one or more olefinic compounds in the absence of hydrogen.

27. The method of claim 11, wherein the method further comprises converting the olefinic compounds to a synthetic fossil fuel by contacting said olefinic compounds, at a temperature of at least 100° C. and up to 500° C., to an additional catalyst capable of converting the olefinic compounds to a synthetic fossil fuel.

* * * * *